United States Patent [19]

Lee, Jr.

[11] 4,260,701

[45] Apr. 7, 1981

[54] FORMULATION FOR SELF-CURING ARTIFICIAL FINGERNAILS CONTAINING METHOXYETHYL METHACRYLATE

[75] Inventor: Henry L. Lee, Jr., Pasadena, Calif.

[73] Assignee: Lee Pharmaceuticals, S. El Monte, Calif.

[21] Appl. No.: 148,735

[22] Filed: May 12, 1980

[51] Int. Cl.³ .......................................... C08F 265/06
[52] U.S. Cl. ............................... 525/303; 260/17 A; 260/42.52; 424/61; 428/500; 525/79; 525/259; 525/939; 260/31.2 MR
[58] Field of Search ............... 525/303, 259, 939; 526/320; 260/17 A, 31.2 M; 424/61

[56] References Cited

U.S. PATENT DOCUMENTS

| | | | |
|---|---|---|---|
| 2,654,717 | 10/1953 | Rehberg et al. | 526/320 |
| 3,539,533 | 11/1970 | Lee et al. | 260/47 |
| 3,647,498 | 3/1972 | Dougherty | 117/8 |
| 4,104,333 | 8/1978 | Lee et al. | 525/309 |

*Primary Examiner*—Carman J. Seccuro
*Attorney, Agent, or Firm*—Irons and Sears

[57] ABSTRACT

Improved composition for a fingernail coating having an acrylic binder, a peroxide catalyst, a tertiary amine accelerator, and a polymeric filler at least partially soluble in the coating. The acrylic binder contains a monoethylenically unsaturated monomer comprising at least a major proportion of methoxyethyl methacrylate. A polyfunctional monomer may be present that copolymerizes with the monoethylenically unsaturated monomer, for crosslinking and toughening.

18 Claims, No Drawings

FORMULATION FOR SELF-CURING ARTIFICIAL FINGERNAILS CONTAINING METHOXYETHYL METHACRYLATE

FIELD OF THE INVENTION

This invention relates to compositions useful for forming coatings on human nails. More particularly, the invention relates to self-curing coatings that can be applied to human nails to form decorative and protective coatings, and/or artificial fingernails.

BACKGROUND OF THE INVENTION

Artificial nail compositions are described in U.S. Pat. No. 4,104,333, granted Nov. 15, 1977, and assigned to Lee Pharmaceuticals. In these compositions, the curable binder is a combination of at least two monomers, one of which is a monofunctional acrylate, preferably either tetrahydrofurfuryl acrylate or tetrahydrofurfuryl methacrylate, and the other of which is a polyfunctional carboxylate.

Formulating such an artificial nail coating composition is very challenging. The composition must be curable, once mixed, within a time period that is acceptable to the consumer. As a practical matter this means that curing must occur within about 120 to about 400 seconds after mixing and application. In addition, for greatest convenience and acceptability, curing must occur under ambient conditions to which the nail is normally exposed including ambient temperature and normal atmospheric conditions.

When cured, the coating must have sufficient adhesion to the substrate nail to resist mechanical removal. It must be strong and hard, like the natural nail. At the same time, it must be sufficiently flexible so that it can withstand the normal stresses to which human nails are ordinarily subjected, without cracking or breaking, and it must be removable at will in a reasonably convenient way.

Formulating a nail coating composition or artificial nail composition that has all of these characteristics, especially freedom from brittleness, is very difficult. In U.S. Pat. No. 4,104,333, certain dibenzoates and phthalates or diphthalates are suggested for use as flexiblizers. Such components add to the cost of the formulation, and while imparting a certain degree of flexibility, dilute the binder and filler, and thus require an added degree of formulating skill to balance the proportions of the ingredients in order to obtain the desired physical characteristics in the cured article.

BRIEF SUMMARY OF THE INVENTION

This invention is concerned with compositions that are suitable for application to the nails, especially human fingernails, that cure rapidly, after application, under ambient conditions. These compositions may be used as decorative coatings to mend natural and artificial nails, or to create artificial fingernails.

Compositions in accordance with the present invention have a liquid resin binder comprising an acrylic resin; a peroxide catalyst-tertiary amine accelerator curing system; and polymeric filler that is at least partially soluble in the composition. The liquid resin binder comprises a monofunctional monomer comprising methoxyethyl methacrylate, and may also contain a polyfunctional carboxylate that is copolymerizable with the monofunctional monomer and that serves as a cross-linker.

DETAILED DESCRIPTION OF THE INVENTION

Generally, the invention embraces compositions suitable for application to a fingernail as a hardenable coating or to form an artificial nail, having a particular kind of acrylic binder, a peroxide catalyst and t-amine accelerator curing system, and containing polymeric filler that is at least partially soluble in the composition. The composition is formulated and the catalyst and the accelerator are present in such quantities to cause self-curing to occur in situ, preferably within about 400 seconds after mixture of the ingredients and application to a nail, under ambient conditions to which the nail is normally exposed. The acrylic binder consists of a mixture of the following ingredients, by weight based on the total weight of the acrylic binder:

(a) from about 0% to about 20% of a polymerizable, ethylenically polyunsaturated monomer that can form a cross-linked polymer upon polymerization during curing of the composition, which monomer contains in its molecule at least two groups that are capable of being addition polymerized upon contact with a peroxide-type free radical initiator and a tertiary amine-type accelerator, the polymerizable groups being members of the group consisting of allyl, acryloyl, methacryloyl, and combinations thereof, and (b) a second monomer that is monoethylenically unsaturated, in an amount from about 80% up to about 100%, that copolymerizes with the first monomer upon self-curing of the composition to form a copolymeric structure that is cross-linked, the second monomer comprising in major proportion methoxyethyl methacrylate.

Preferably, the acrylic binder consists of from about 0% to about 15% of a cross-linkable monomer such as one selected from the group consisting of ethylene glycol dimethacrylate, diethylene glycol dimethacrylate, triethylene glycol dimethacrylate, polyethylene glycol dimethacrylate, tris-propylene glycol dimethacrylate, and mixtures thereof, that are capable of being polymerized upon contact with a peroxide-type free radical initiator and a t-amine-type accelerator; and from about 85% to about 100% of methoxyethyl methacrylate. When the cross-linkable monomer forms up to 20% of the acrylic binder, the set time is easily adjusted to be within desired limits, through adjustment of the amounts of catalyst and accelerator; when it is in the range from 0% to 15%, the desired physical properties are more readily obtained. A polymeric filler, preferably one soluble in the monomer, is generally added to produce a coating composition that cures to have desired physical properties. A high loading with a polymeric filler often will produce a cured coating having properties within desired limits even when little or no cross-linker is employed.

The formulation should preferably be such that after curing, it exhibits a flexible modulus of rupture of at least 500 kgs./cm$^2$; a flexural yield strength of at least 500 kg./cm$^2$; a flexural modulus of elasticity of at least 15,000 to about 50,000 kgs./cm$^2$; and a Rockwell R hardness of at least 75.

Compositions made in accordance with the present invention are characterized by the use of a particular kind of monoethylenically unsaturated acrylic monomer alone or in combination with other compatible monoethylenically unsaturated monomers, as the monoethylenically unsaturated component of the liquid resin binder. One monomer, which is essential, is methoxyethyl methacrylate. It preferably furnishes the major amount of the monoethylenically unsaturated monomer present, but it may be mixed with other compatible monoethylenically unsaturated monomer(s) that are suitable, such as, for example, tetrahydrofurfuryl acrylate and/or methacrylate. The other monomer, if used, is one that can copolymerize with the first monomer and that will modify the properties of the cured monomer mixture and/or effect cross-linking.

The preferred polyfunctional monomers are selected from the group consisting of ethylene glycol dimethacrylate, diethylene glycol dimethacrylate, triethylene glycol dimethacrylate, polyethylene glycol dimethacrylate, trispropylene glycol dimethacrylate, and mixtures thereof. Of these, tris-propylene glycol dimethacrylate and diethylene glycol dimethacrylate are ordinarily most preferred. Unfortunately, tris-propylene glycol dimethacrylate is not readily available, so that diethylene glycol dimethacrylate is the polyfunctional monomer most commonly used in the formulations described herein. While its use tends to impart stiffness, overall strength at a given concentration is increased. These monomers impart flexural strength to the cured coatings.

Among the other polyfunctional monomers herein contemplated are 2,2 bis[4'-(3"-methacryloyl-2"-hydroxypropoxy)phenyl] propane (bis GMA); tetraethylene glycol dimethacrylate; 2,2 bis (4'-methacryloyl phenyl) propane; bis(2-methacryloylethyl) o-, m-, and p-phthalates; 2-acryloylethylmethacrylate, and methacrylate terminated urethanes.

Other similar polyfunctional monomers having at least two groups or moieties such as allyl, acryloyl, methacryloyl or other similar unsaturations, capable of polymerizing in the presence of the initiators and accelerators of the present invention, are herein contemplated. Typically, these monomers are not only mono-polymerizable and copolymerizable, but they are suitable cross-linking agents for the monofunctional monomers specified above.

Certain mixtures of these polyfunctional monomers may also be used if desired. For example, a mixture of allyl methacrylate and 2,2 bis[4'(-3"-methacryloyl-2"-hydroxypropoxy)phenyl] propane (bis GMA) with a mixture of diethylene glycol and triethylene glycol dimethacrylates is useful. Similarly, a mixture of diallyl phthalate and diethylene glycol dimethacrylate is useful.

The essential monofunctional monomer, methoxyethyl methacrylate, or a mixture thereof with a minor amount of another compatible, suitable diluent monomer, is characterized by its ability to polymerize to form polymers of a substantial hardness but, surprisingly, superior flexibility, whether polymerized alone or in combination with polyfunctional monomer. The preferred "essential" monofunctional monomer is methoxyethyl methacrylate alone.

Generally the monofunctional monomer component of the binder is provided in major part or in its entirety by methoxyethyl methacrylate. Any dermatologically acceptable acrylate or methacrylate monomer may be used as a diluent for the methoxyethyl methacrylate, provided the resulting properties of the cured coating composition are acceptable. Among the diluents that have been used are tetrahydrofurfuryl methacrylate and acetol methacrylate. In addition, many of the family of alkoxy alkyl methacrylates are useful diluents, especially the lower alkoxy, lower alkyl methacrylates. Any dermatologically acceptable monomer known to have fairly brittle properties after curing would serve to strengthen a formulation based on methoxyethyl methacrylate. Conversely, the methoxyethyl methacrylate can be regarded as serving to modify the brittle properties of any other monomer that might be selected as a diluent.

Generally, the polyfunctional monomer should provide up to about 20% by weight of the total resin present, and the essential monofunctional monomer forms the balance. Although no polyfunctional monomer need be present in the liquid resin binder, it is preferred that it comprise at least 5% of the resin binder. The resin binder is defined as the curable monomer(s) present.

The curing systems generally are those recognized in the art, and may be used in art-recognized amounts. The preferred initiators or catalysts are the free radical catalysts, particularly the organic peroxides. Of these, benzoyl peroxide and lauroyl peroxide are preferred. Benzoyl peroxide is the preferred initiator, and it is usually employed at a concentration of about 0.2% to about 4% by weight of the resin binder.

The accelerators preferably are tertiary amines, especially N,N-di(lower)alkyl-p-toluidines (e.g., N,N-dimethyl-p-toluidine, N,N-diethyl-p-toluidine) and N,N-di (lower) alkyl anilines, such as N,N-dimethyl aniline. The preferred accelerator is N,N-dihydroxyethyl-p-toluidine, and it is usually employed at a concentration of about 0.1% to about 8% by weight of the resin binder.

Of course, other conventional, compatible free-radical catalysts and promoters, while not at present preferred, may be used in lieu of or in conjunction with the foregoing.

A polymeric filler material is generally incorporated in the formulation, in finely divided form. It may be soluble or partially insoluble in the coating composition.

The composition is usually packaged in two portions that are mixed for use. These may be, for example, a liquid and a powder, or a paste and a paste. The particulate polymeric filler may be packaged with either component or may be divided between the two. The preferred polymeric filler materials include the copolymers of methyl and ethyl methacrylates; and the polymers and copolymers generally of the lower alkyl acrylates and methacrylates, with the lower alkyl methycrylate esters being preferred. The polymeric filler is generally present in an amount in the range from about 5% to about 75% by weight of the coating composition; more or less of any particular filler may be used, depending on the properties desired.

Other components that ordinarily will be used include minor amounts of such materials as dyes, opaquing agents such as titanium dioxide, and stabilizers such as 3-butyl-4-hydroxy toluene. A U.V. absorber could be included but is not necessary.

In a preferred embodiment of the invention, the coating composition is packaged as a liquid and a powder. These are mixed together to form a coating composition at the time of use. Ordinarily, with this two package system, the catalyst is packaged separately from the monomer system. The accelerator may be with the monomer system or in the package with the catalyst (separate from the monomer). The proportions in which the two packages are blended together may be selected at a convenient level, which generally will be in the range from about 3 to 1 to about 1 to 3, and preferably, about 1 liquid to 2 powder, by weight.

Coating compositions prepared in accordance with the present invention should, for consumer acceptance, convenience, and other practical reasons, set within about 120 seconds to about 400 seconds. The setting time may be adjusted by regulating the concentrations of the catalyst and accelerator respectively. Often only the proportion of accelerator need be increased, to obtain a faster setting time.

In addition to the essential and preferred components of the coating compositions of this invention described above, other ingredients may also be used, such as an inorganic filler material. This could be, for example, finely divided alumina, silica, quartz, glass, aluminum silicate, or the like, which are all useful in adjusting the consistency of the coating composition and for improving its physical and mechanical properties.

The invention will now be further described in the following specific examples in which several demonstrations of the invention are described in some detail. All parts and percentages are by weight unless expressly stated to be otherwise, and temperatures are in degrees Celsius.

EXAMPLES

Self-Curing Artificial Fingernails

The formulations described below in Table 2 were prepared and observed for performance, including flexural strength and hardness. Each formulation included a liquid component, whose composition is described in Table 2, and a powder component, whose composition is described in Table 3.

The liquid component was prepared to include monoethylenically unsaturated monomer, often together with ethylenically polyunsaturated monomer, and accelerator, stabilizer, polymeric filler, and dye concentrate. The polymeric filler in the liquid component is preferably a polymethacrylate, and it must be free from residual initiator if it is to be incorporated in the liquid component along with the accelerator. Any benzoyl peroxide present in the polymethacrylate is conveniently removed by baking the polymethacrylate filler prior to use.

The liquid component is conveniently prepared by heating the monomer(s) with constant stirring to 40° C. to 45° C. (35° C. was used for Exs. 13–16). Each other component is then added, with stirring until each has completely dissolved. The polymeric filler is added last, without interruption of the heating and stirring until complete dissolution has been achieved.

The dye concentrate used in most of the liquid components is conveniently prepared in somewhat similar fashion, to facilitate blending. It generally has a monomer component, and contains accelerator, stabilizer, and one or more dyes. The monomer component is heated to 40° C. to 45° C., with stirring, and the other ingredients are then added (in the order listed below). Stirring and heating are continued until dissolution is complete.

In the following examples, three different dye concentrate formulations were used, described below in Table 1:

TABLE 1

| Ingredients | Dye Concentrates #1 | #2 | #3 |
|---|---|---|---|
| Methoxy Ethyl Methacrylate | 100 | 90 | 90 |
| Diethyleneglycoldimethacrylate | 0 | 10 | 10 |
| N,N-dihydroxyethyl-p-toluidine | 2.0 | 2.0 | 0 |
| Butylated Hydroxy Toluene | 0.06 | 0.06 | 0.06 |
| D&C Red #17 | 0.16 | 0.16 | 0.1 |
| D&C Red #37 | 0.16 | 0.16 | 0 |
| D&C Violet #2 | 0 | 0 | 0.04 |

The dyes are present for cosmetic purposes, and play no material role in the physical properties of the artificial fingernail material.

In each example, the liquid and powder components were mixed in the proportion of 1 to 2 by weight, respectively, then cured for 24 hours at room temperature before testing. Setting times are reported where they were observed.

TABLE 2

| | Liquid Components, Parts by Weight | | | | | | |
|---|---|---|---|---|---|---|---|
| Example | Methoxyethyl Methacrylate and other monoethylenically unsaturated monomer T | Polyfunctional carboxylate | N,N bis (2-hydroxyethyl) p-toluidine | Poly (methyl methacrylate) | 3-butyl-4-hydroxy-toluene | Dye Concentrate, No. + pph** | Powder Component |
| 1 | 100 | — | 2.5 | 4.5 | 0.06 | 1–0.4 | A |
| 2 | 90 | 10-DEGDMA | 2.5 | 4.5 | 0.06 | 2–0.4 | A |
| 3 | 90 | 10-BIS/GMA | 3.2 | 4.0 | 0.06 | 0.1 dye*** | A |
| 4 | 100 | — | 2.5 | 4.5 | 0.06 | 1–0.4 | B |
| 5 | 90 | 10-DEGDMA | 2.5 | 4.5 | 0.06 | 2–0.4 | B |
| 6 | 100 | — | 2.5 | 4.5 | 0.06 | 1–0.4 | C |
| 7 | 90 | 10-DEGDMA | 2.5 | 4.5 | 0.06 | 2–0.4 | C |
| 8 | 90 | 10-DEGDMA | 4.0 | 4.5 | 0.06 | 3–0.6 | D |
| 9 | 90 | 10-DEGDMA | 3.2 | 4.5 | 0.06 | 3–0.6 | E |
| 10 | 100 | — | 2 | — | 0.06 | — | F |
| 11 | 90 | 10-DEGDMA | 2 | — | 0.06 | — | F |
| 12 | 80 | 20-DEGDMA | 2 | — | 0.06 | — | F |
| 13 | — 90T | 10-DEGDMA | 2.5 | 4.5 | 0.06 | — | B |
| 14 | 30 60T | 10-DEGDMA | 2.5 | 4.5 | 0.06 | — | B |
| 15 | 60 30T | 10-DEGDMA | 2.5 | 4.5 | 0.06 | — | B |
| 16 | 90 | 10-DEGDMA | 2.5 | 4.5 | 0.06 | — | B |
| 17 | 90 | 10-DEGDMA | 3.0 | 6.0 | 0.06 | — | B |

TABLE 2-continued

| | | | | | | | |
|---|---|---|---|---|---|---|---|
| 18 | 90 | 10-BIS/GMA | 3.0 | 6.0 | 0.06 | — | B |

**pph: parts per hundred of the liquid.
***0.06 D&C Red #17 and 0.06 D&C #37; mixed directly into the liquid.
T: Tetrahydrofurfuryl methacrylate

| | Physical Properties* | | | |
|---|---|---|---|---|
| Example | Flexural Strength | $E_B$ | Rockwell "R" Hardness | Set Time. Seconds |
| 1 | 370 [2] | 15,566 | 53 | 250–380 |
| 2 | 852 [2] | 29,502 | 94 | 270 |
| 3 | 766 [2] | 27,298 | 89 | 209 |
| 4 | 306 [2] | 11,632 | 44 | — |
| 5 | 724 [2] | 28,596 | 76 | — |
| 6 | 119 [3] | 7,855 | 16 | — |
| 7 | 584 [2] | 25,880 | 82 | — |
| 8 | — | — | — | 220 at 21° C. |
| 9 | — | — | — | 150 at 25° C. |
| 10 | 332 [2] | 12,100 | 66 | 215 |
| 11 | 630 [1] | 21,432 | 92 | — |
| 12 | 766 [1] | 25,786 | 100 | — |
| 13 | 796 [1] | 35,375 | — | — |
| 14 | 1313 [1] | 49,887 | — | — |
| 15 | 743 [1] | 32,174 | — | — |
| 16 | 753 [2] | 25,563 | — | — |
| 17 | — | — | — | — |
| 18 | — | — | — | — |

*Each value reported is average from values observed on several specimens.
[1] Modulus of Rupture; approximate values.
[2] Yield strength.
[3] Test terminated before yield or rupture was obtained.

Glossary

| | |
|---|---|
| Flexural Strength (Modulus of Rupture): | units, kg/cm$^2$; formula used, $S = \dfrac{3WL}{2bd^2}$; Where S is the stress in the outer (theoretical) fiber of the specimen at midspan, in Kg/cm$^2$; W is the load applied at the point of structural failure in Kg.; L is the span in cm.; b is the width of cm., and d is the thickness in cm. |
| Yield Strength: | derived from the same curve as flexural strength (modulus of rupture), but at a different point, i.e., a different mode of failure. |
| Flexural Modulus: | $E_B = \dfrac{L^3W}{4bd^3y}$ in $\dfrac{Kg.}{cm^2}$ where L, W, b, and d are as above, and y is the maximum vertical deflection of the beam, in cm. specimens for flexural strength and flexural modulus; L = 2.54 cm. b = 1 cm. d = 0.2 cm. evaluated on an Instron instrument. |
| Rockwell Hardness: | specimen, 2 mm × 25 mm diam. |
| DEGDMA | diethylene glycol dimethacrylate |

TABLE 3

Powder Compositions

| Component | Parts by Weight | | | | | |
|---|---|---|---|---|---|---|
| | A | B | C | D | E | F |
| 30/70 copolymer of methyl and ethyl methacrylates (a) impregnated with 2.6% by weight benzoyl peroxide | 75 | 70.5 | — | 50 | 50 | — |
| (b) not impregnated | 25 | 23.5 | — | 50 | 50 | — |
| copolymer powder* (flexibilizer) | — | 6 | 6 | — | — | — |
| titanium dioxide (opaquing agent) | 0.05 | 0.05 | 0.05 | 0.1 | 0.05 | — |
| polymethyl methacrylate, impregnated with 2.6% by weight benzoyl peroxide | — | — | 94 | — | — | 100 |

*A commercially available, particulate block copolymer of methyl methacrylate, sytrene, and butadiene, in a 1:1:1 monomer ratio.

Example 2 compared favorably in strength with a currently commercially available formulation, and exhibited superior flexibility.

Generally the setting times for Examples 1 through 7 were considered somewhat slow for use in artificial fingernail compositions, indicating the need for higher levels of catalyst and initiator for this particular application. Example 8 was prepared to have a more acceptable set time for fingernail application, and it did. The values reported are satisfactory. The color and opacity of Example 8 cured coatings were also acceptable.

Example 9 was prepared with a view toward balancing the proportions of the respective components so as to obtain acceptable properties and costs for artificial fingernail use.

As is clear from the examples, the physical properties observed with Examples 1 through 7 (which have polymeric filler) indicate products that are well suited for the intended use.

Example 13 describes a prior art composition; it is within the teachings of U.S. Pat. No. 4,104,333 and is generally similar to the compositions of Exs. VII and VIII of that patent. The physical properties of cured test specimens prepared according to Exs. 13-16 were further evaluated and are reported below in Table 4. The results indicate no impediment to the preparation of formulations where a minor proportion of the monoethylenically unsaturated monomer is tetrahydrofurfuryl methacrylate.

be used to thicken the liquid part include: ethylhydroxyethyl cellulose; vinyl toluene/alpha methyl styrene copolymer; polyvinyl acetate; methacrylate-butadiene-styrene copolymer; and ethyl cellulose. Generally these materials may be used in the same proportions as other polymeric fillers in the liquid part, i.e., about 4 parts to about 10 parts by weight per 100 parts of total monomer.

The invention is further demonstrated by the following examples in Table 5, in which Ex. 19 is presented for comparative purposes.

TABLE 5

| Liquid Component | Example No. | | | | | |
|---|---|---|---|---|---|---|
| | 19 | 20 | 21 | 22 | 23 | 24 |
| Methoxyethyl methacrylate | — | 90 pbw | 90 pbw | 95 pbw | 90 pbw | 90 pbw |
| Diethyleneglycol dimethacrylate | 100 pbw | 10 | — | — | — | — |
| Triethyleneglycol dimethacrylate | — | — | — | — | 10 | — |
| Polyethyleneglycol dimethacrylate | — | — | — | — | — | 10 |
| Bisphenol A diglycidyl dimethacrylate | — | — | 10 | — | — | — |
| Bisphenol A Dimethacrylate | — | — | — | 5 | — | — |
| Butylated hydroxy toluene | 0.06 | 0.06 | 0.06 | 0.06 | 0.06 | 0.06 |
| N,N-dihydroxyethyl-p-toluidine | 2.5 | 3.0 | 3.0 | 2.5 | 2.5 | 2.5 |
| Polymethyl methacrylate, baked | — | 6.0 | 6.0 | 6.0 | 6.0 | 6.0 |
| Ethyl cellulose | 4.5 | — | — | — | — | — |
| Powder component[1] | G | H | H | H | H | H |
| Flexural Properties | | | | | | |
| Proportional Limit (Kg/cm$^2$) | 314 | 542 | 458 | 433 | 612 | 537 |
| Modulus of Elasticity (Kg/cm$^2$) | 44396 | 41020 | 44834 | 38722 | 37360 | 31566 |
| Modulus of Rupture (Kg/cm$^2$) | 1195* | 1089* | 1147* | — | 1003* | 974* |
| Yield Strength (Kg/cm$^2$) | 1195* | 1089* | 1147* | 909 | 1003* | 974* |

[1] See TABLE 6 below for the compositions of powders G and H.
*The test was terminated before rupture or yield was obtained.

The powder formulations used had the compositions indicated in Table 6 below.

TABLE 6

| | Powder Composition, PBW | |
|---|---|---|
| | G | H |
| copolymer of methyl and ethyl methacrylates: | | |
| (a) impregnated with 2.5% benzoyl peroxide | 25 | 50 |
| (b) not impregnated but containing about 0.6% benzoyl peroxide | 75 | 50 |

TABLE 4

| | Mechanical Properties, Exs. 13-16 | | | | | |
|---|---|---|---|---|---|---|
| Example | Storage conditions 24 hrs at | Yield Point | Yield Strength $S = \frac{3WL}{2bd^2}$ | Elastic Modulus $E_B = \frac{L^3 m}{4bd^3}$ | Diametral Compressive Yield Point | Rockwell "F" Hardness |
| 13 | R.T. | 4.2 Kg | 796 Kg/cm$^2$ | 35375 Kg/cm$^2$ | — | — |
| | 37° C./H$_2$O | 3.7 | 804 | 27274 | 136 Kg | 56 |
| 14 | R.T. | 6.2 | 1313 | 49887 | — | — |
| | 37° C./H$_2$O | 2.2 | 620 | 25562 | 159 | 50 |
| 15 | R.T. | 3.6 | 743 | 32174 | — | — |
| | 37° C./H$_2$O | 2.0 | 536 | 21795 | 148 | 39 |
| 16 | R.T. | 3.5 | 753 | 25563 | — | — |
| | 37° C./H$_2$O | 1.8 | 454 | 16140 | 120 | 24 |

The materials stored at room temperature (R.T.) out of water were much stiffer than those stored in water at 37° C. Since most artificial nails would be subjected to room temperature ambient conditions (dry), the physicals observed under these conditions are probably more significant than the others.

The liquid portion formulations of Exs. 17 and 18 can be evaluated with any of the powder mixes described in Table 3, or with others. The relatively high content of polymeric filler goes into solution in the monomer, and thickens the liquid somewhat. Other materials that can Each liquid portion was prepared by dissolving, or attempting to dissolve, the solid materials in the mildly heated liquid mixture with constant stirring. The powders were prepared by weighing the appropriate amounts of powder into a jar, capping, and shaking for about 1/8 hour. The flexural samples were prepared by mixing 1 g. liquid with 2 g. powder and casting flexural molds in a standard fashion, employed throughout all tests reported therein. The specimens were allowed to cure at room temperature for approximately 24 hours. Flexural tests were then performed according to a standard test method.

The liquid/powder mix of Ex. 19 was somewhat dry, and the resulting material was somewhat opaque, indicating a degree of insolubility of the polymeric powder in the liquid. The polymerized material was stronger and stiffer than most of the other materials tested.

Except for Ex. 22, all of the materials tested seemed a little too stiff. This may be caused by the polymeric filler. The mixtures were useful coating compositions, however.

Still further demonstrations of the invention are reported in Table 7 below. The procedures described above were followed in carrying out these demonstrations.

bisphenol A dimethacrylate contributed to increasing brittleness. The formulations of Examples 31 and 32 had good flexural properties, and the elastic moduli and yield strengths were of interest, especially because no crosslinking resin was used.

In the following demonstrations of the invention reported in Table 8, the effects of different polymeric fillers in the liquid portion were investigated, following the preparatory procedures already described.

The polymeric fillers examined were methacrylateacrylonitrile-butadiene-styrene copolymer (M-A-B-S), acrylonitrile-butadiene-styrene copolymer (A-B-S), poly (butyl) methacrylate, butyl/isobutyl methacrylate copolymer, poly (ethyl) methacrylate, styrene/methyl methacrylate copolymer, and methyl/ethyl methacrylate copolymer. Depending on the ease with which they

TABLE 7

| Liquid Component | Example No. | | | | | | | |
|---|---|---|---|---|---|---|---|---|
| | 25 | 26 | 27 | 28 | 29 | 30 | 31 | 32 |
| Methoxyethyl methacrylate | 90 pbw | 90 pbw | 90 pbw | 80 pbw | 90 pbw | 90 pbw | 100 pbw | 100 pbw |
| Diethyleneglycol dimethacrylate | 10 | 10 | — | — | 10 | 10 | — | — |
| Bis-phenol A dimethacrylate | — | — | 10 | 20 | — | — | — | — |
| Butylated hydroxy toluene | 2.5 | 2.5 | 2.5 | 2.5 | 2.5 | 2.5 | 2.5 | 2.5 |
| Polymethyl methacrylate, baked | 5.0 | 7.0 | 5.0 | 5.0 | 8.0 | 9.0 | 15.0 | 10.0 |
| Powder | H | H | H | H | H | H | H | H |
| Set time (seconds @ 23.5° C.) | 220 | 240 | 200 | 160 | 220 | 220 | 250 | 290 |
| Flexural Properties | | | | | | | | |
| Proportional limit (Kg/cm$^2$) | 613 | 528 | 484 | 730 | 450 | 502 | 352 | 344 |
| Modulus of elasticity (Kg/cm$^2$) | 33288 | 29040 | 31168 | 33360 | 33441 | 29805 | 26000 | 24370 |
| Modulus of rupture (Kg/cm$^2$) | — | — | — | 1126 | — | — | — | — |
| Yield Strength (Kg/cm$^2$) | 1089 | 960 | 1068 | — | 1068 | 996 | 749 | 746 |

In Examples 25 through 32 as reported above in Table 7, flexural properties and set times were evaluated for methoxyethyl methacrylate formulations containing 10% diethyleneglycol dimethacrylate as cross-linker and 5–9% polymethyl methacrylate as filler, and 10–20% bisphenol A dimethacrylate as cross-linker and 5% polymethyl methacrylate as filler. Also evaluated were non-crosslinked formulations containing 10% and 15% polymethyl methacrylate as filler. Table 7 summarizes the formulations and their respective observed properties.

It is difficult to draw conclusions from the formulations of these examples because the results of flexural tests can vary plus or minus 10%. Considering such variations, many of the formulations tested appear to have essentially the same flexural properties. The only trend apparently established was for the formulations of Examples 27 and 28, where increasing concentraitons of dissolved, they were used at levels of 5–10 parts per hundred resin. M-A-B-S and A-B-S solutions were milky white dispersions. The poly (butyl) methacrylate appeared to swell up rather than dissolve; this could have been caused because the polymer was in the form of unpulverizable beads rather than a fine powder. All the other polymer powders dissolve fairly readily.

Flexural samples were prepared as described earlier with 1 g of the liquid formulation mixed with 2 g. of powder. The flexural samples were allowed to cure at room temperature for 18–24 hours and were tested on the Instron according to a standard test method.

Table 8 summarizes the formulations and respective properties. The formulation of Example 37 showed a very high proportional limit, and also a high elastic modulus. The formulation of Example 38 was interesting had a fairly high proportional limit with a more flexible elastic modulus.

TABLE 8

| Liquid Portion | Example No. | | | | | | | |
|---|---|---|---|---|---|---|---|---|
| | 33 | 34 | 35 | 36 | 37 | 38 | 39 | 40 |
| Methoxyethyl methacrylate | 100 pbw | 90 pbw | 100 pbw | 90 pbw | 90 pbw | 95 pbw | 90 pbw | 90 pbw |
| Diethyleneglycol dimethacrylate | — | 10 | — | 10 | 10 | 5 | 10 | 10 |
| Butylated hydroxy toluene | .06 | .06 | .06 | .06 | .06 | .06 | 0.06 | 0.06 |
| N,N-dihydroxyethyl-p-toluidine | 2.5 | 2.5 | 2.5 | 2.5 | 2.5 | 2.5 | 2.5 | 2.5 |
| M-A-B-S copolymer[1] | 5.0 | — | — | — | — | — | — | — |
| A-B-S copolymer[2] | — | — | 5.0 | — | — | — | — | — |
| Poly (isobutyl/butyl) methacrylate[3] | — | 8.0 | — | — | — | — | — | — |
| Poly (ethyl) methacrylate[3] | — | — | — | 8.0 | 10.0 | — | — | — |
| Poly (methyl) methacrylate, baked | — | — | — | — | — | 10.0 | — | — |
| Poly (methyl/ethyl) methacrylate[4] | — | — | — | — | — | — | — | 10.0 |
| Styrene/methyl methacrylate copolymer[5] | — | — | — | — | — | — | 8 | — |
| Flexural Properties | | | | | | | | |
| Proportional limit (Kg/cm$^2$) | 318 | 514 | 308 | 484 | 520 | 470 | 480 | 446 |
| Modulus of elasticity (Kg/cm$^2$) | 20365 | 32624 | 23347 | 28962 | 32030 | 29726 | 33170 | 32158 |

TABLE 8-continued

| Liquid Portion | Example No. | | | | | | | |
|---|---|---|---|---|---|---|---|---|
| | 33 | 34 | 35 | 36 | 37 | 38 | 39 | 40 |
| Yield strength (Kg/cm²) | 642 | 1010 | 698 | 934 | 1032 | 905 | 1080 | 976 |

[1] methacrylate-acrylonitrile-butadiene-styrene copolymer; Borg-Warner
[2] acrylonitrile-butadiene-styrene copolymer; Borg-Warner
[3] Aldrich Chemical Co.
[4] baked 30/70 methyl/ethyl methacrylate copolymer; Esschem
[5] Esschem A different powder component was employed in the demonstrations of the invention reported in Table 9 below. The liquid formulation of Example 38 was combined with polyethyl methacrylate as the powder component, in Example 42.

Powder component I was prepared by pulverizing 0.64 g. of benzoyl peroxide (BP0) with 42 g. polyethyl methacrylate, sifting the material through a nylon mesh, and then mixing thoroughly by shaking in a closed container. The resultant powder contained 1.5% BPO. Flexural properties of some liquid/powder mixtures, using powder I, and prepared in the usual 1:2 proportions, are summarized in Table 9. Powder I imparted generally weaker properties than powdered polymethyl/ethyl methacrylate containing about 1.5% BPO.

The "Special Adduct" employed in Examples 43 and 44 as a cross-linker is an adduct of hydroxypropyl methacrylate and trismethylhexamethylene diisocyanate. It is a viscous liquid and is a poor solvent for the polymeric filler, indicating the desirability of incorporating a diluent dimethacrylate in such formulations.

In addition to hydroxypropyl methacrylate, other hydroxyalkyl methacrylates may be employed to form similarly useful adducts. The hydroxy-lower-alkyl methacrylates are preferred. Also, many different diisocyanates may be used in making useful adducts. Generaly those with aliphatic backbones are preferred.

CONCLUSION

After curing, coating compositions prepared in accordance with the invention can be formulated to have, particularly when formulated according to the preferred embodiments exemplified by Examples 2, 3, 5, 7, 8 and 9, respectively, a flexural modulus of rupture of at least 500 kg./cm²; a flexural yield strength of at least 500 kg./cm²; a flexural modulus of elasticity of 15,000–50,000 kg./cm²; and a Rockwell R hardness of at least 75 up to about 100. In addition, they should produce, if properly formulated to do so, an in vivo adhesion to natural human nails of at least about 90 psi 6.3 kg/cm²), preferably about 100 psi 7.0 kg/cm²), with maximum values generally in the range from about 150 psi to about 200 psi (10.5 to 14.0 kg/cm²).

When an inorganic filler is incorporated in a formulation, ordinarily it will be used in an amount in the range from about 2% to about 10% by weight of the overall composition. Such a filler should have an average particle size of not more than about 60 microns in diameter, the term diameter referring to the largest dimension of the particle as is conventional.

While the invention has been disclosed herein by reference to the details of preferred embodiments

TABLE 9

| Liquid Component | Example No. | | | | | |
|---|---|---|---|---|---|---|
| | 41A | 41B | 42A | 42B | 43 | 44 |
| methoxyethyl methacrylate | 90 | 90 | 95 | 95 | 80 | 90 |
| diethyleneglycol dimethacrylate | 10 | 10 | 5 | 5 | — | — |
| Special Adduct* | — | — | — | — | 20 | 10 |
| butylated hydroxytoluene | 0.06 | 0.06 | 0.06 | 0.06 | 0.06 | 0.06 |
| N,N-bis dihydroxyethyl-p-toluidine | 2.5 | 2.5 | 2.5 | 2.5 | 2.5 | 2.5 |
| polymethyl methacrylate, baked | — | — | 10 | 10 | 10 | 10 |
| polyethyl methacrylate | 10 | 10 | — | — | — | — |
| Powder | H | I | H | I | H | H |
| Flexural Properties | | | | | | |
| proportional limit (Kg/cm²) | 520 | 442 | 470 | 427 | 511 | 454 |
| elastic modulus (Kg/cm²) | 32,030 | 27,764 | 29,726 | 24,440 | 33,793 | 29,158 |
| yield strength (Kg/cm²) | 1,032 | 863 | 905 | 808 | — | 890 |
| modulus of rupture (Kg/cm²) | — | — | — | — | 987 | — |

*N,N'-Bis(3-methacryloxymethylethoxycarboxy)-trimethyl-hexane-1,6-diamine; representative nomenclature.

Instead of one of those polyunsaturated monomers indicated in the examples, any one of the following may be used, with suitable formulating adjustments to obtain desired properties: a polyethylene glyol dimethacrylate; triethylene glycol dimethacrylate; a mixture of (1), a blend of alyl methacrylate and bis/GMA, and (2) blend of diethylene glycol and triethylene glycol dimethacrylates; or a mixture of diallyl phthalate and diethylene glycol dimethacrylate. Since triethylene glycol dimethacrylate and polyethylene glycol dimethacrylate tend to generate a high heat of polymerization, they should be used sparingly if at all.

thereof, it is to be understood that such disclosure is intended in an illustrative rather than in a limiting sense, and it is contemplated that various modifications in the compositions of the invention will readily occur to those skilled in the art, within the spirit of the invention and the scope of the appended claims.

What is claimed is:

1. A composition suitable to be applied to a fingernail as a hardenable coating or to form an artificial nail, having an acrylic binder, a peroxide catalyst and t-amine accelerator curing system, and containing polymeric filler that is at least partially soluble in the composition, the composition being formulated and the catalyst and the accelerator being present in a quantity to cause self-curing to occur in situ within about 400 seconds after mixture of the ingredients and application to a nail, under ambient conditions to which the nail is normally exposed, wherein the acrylic binder consists of a mixture of the following ingredients, by weight based on the weight of the acrylic binder:
  (a) a first monomer component consisting of from about 0% to about 20% of a polymerizable, ethylenically unsaturated monomer that can form a cross-linked polymer upon polymerization during curing of the composition, which monomer contains in its molecule at least two groups that are capable of addition polymerization upon contact with a peroxide-type free radical initiator and a tertiary amine-type accelerator, the polymerizable groups being members of the group consisting of allyl, acryloyl, methacryloyl, and combinations thereof, and
  (b) a second monomer component consisting of monomer that is monoethylenically unsaturated, in an amount up to about 100%, that copolymerizes with the first monomer component upon self-curing of the composition to form a copolymeric structure that is cross-linked, the second monomer comprising at least a major proportion of methoxyethyl methacrylate.

2. A composition in accordance with claim 1 wherein the (a) monomer is diethylene glycol dimethacrylate.

3. A composition in accordance with claim 1 wherein the (a) monomer is a polyethylene glycol dimethacrylate.

4. A composition in accordance with claim 1 wherein the (a) monomer is triethylene glycol dimethacrylate.

5. A composition in accordance with claim 1 wherein the (a) monomer is 2,2 bis [4'(3''-methacryloyl-2''-hydroxypropoxy)phenyl]propane.

6. A composition in accordance with claim 1 wherein the (a) monomer is an adduct of a hydroxyalkyl methacrylate and a diisocyanate.

7. The composition of claim 6 wherein the (a) monomer is an adduct of hydroxypropyl methacrylate and trismethylhexamethylene diisocyanate.

8. The composition of claim 1, 2, 3, 4, 5, 6 or 7 wherein the second monomer consists essentially of methoxyethyl methacrylate.

9. The composition of claim 1 wherein the acrylic binder consists essentially of methoxyethyl methacrylate.

10. A composition according to claim 1, 2 or 5 that after curing exhibits a flexural modulus of rupture of at least 500 kgs./cm$^2$; a flexural yield strength of at least 500 kg./cm$^2$; a flexural modulus of elasticity of 15,000–50,000 kg./cm$^2$; and a Rockwell R hardness of at least 75.

11. A self-curing composition to be applied to a natural nail as a hardenable coating or to form an artificial nail, having an acrylic binder, a peroxide catalyst and t-amine accelerator curing system, and containing polymer filler that is at least partially soluble in the composition, the composition being formulated and the catalyst and the accelerator being present in a quantity to cause self-curing to occur in situ within about 120 to about 400 seconds after mixture of the ingredients and application to a nail, under ambient conditions to which the nail is normally exposed, wherein the acrylic binder consists essentially of a mixture of the following ingredients, by weight based on the weight of the acrylic binder:
  (a) from about 0% to about 20% of a cross-linkable monomer selected from the group consisting of bisphenol A diglycidyl dimethacrylate (BIS-GMA), bisphenol A dimethacrylate, an adduct of a hydroxyalkyl methacrylate and a diisocyanate, ethylene glycol dimethacrylate, diethylene glycol dimethacrylate, triethylene glycol dimethacrylate, polyethylene glycol dimethacrylate, and mixtures thereof, that are capable of being polymerized upon contact with a peroxide-type free radical initiator and a t-amine-atype peroxide-type free radical initiator and a t-amine-type accelerator; and
  (b) from about 80% to 100% of a monoethylenically unsaturated monomer comprising at least a major proportion of methoxyethyl methacrylate.

12. The composition of claim 11 where the cross-linkable monomer is diethylene glycol dimethacrylate.

13. The composition of claim 12 wherein the monoethylenically unsaturated monomer consists essentially of methoxyethyl methacrylate.

14. The composition of claim 11 wherein the (a) monomer is a poly(alkylene glycol) dimethylacrylate and the acrylic binder consists essentially of methoxyethyl methacrylate.

15. The composition of claim 11, 12, 13 or 14, wherein the composition is packaged in two component portions, a liquid portion and a powder portion, each of which is shelf stable but that form a self-curing composition upon admixture, the liquid portion comprising the acrylic binder, and the powder portion being at least partially soluble in the liquid portion and comprising a polymer formed from at least one monomer having vinyl unsaturation.

16. The composition of claim 15 wherein the polymer in the powder portion is a polymer of a methacrylic acid ester.

17. The composition of claim 15 wherein the maximum amount of (a) monomer is 15%.

18. A self-curing composition to be applied to a natural nail as a hardenable coating or to form an artificial nail, having an acrylic binder, a peroxide catalyst and t-amine accelerator curing system, and containing polymeric filler that is at least partially soluble in the composition, the composition being formulated and the catalyst and the accelerator being present in a quantity to cause self-curing to occur in situ within about 120 to about 400 seconds after mixture of the ingredients and application to a nail, under ambient conditions to which the nail is normally exposed, wherein the acrylic binder consists essentially of a mixture of the following ingredients, by weight based on the weight of the acrylic binder:
  (a) from 0% to about 15% of a crosslinkable monomer comprising 2,2-bis[4'(3''methacryloyl-2''hydroxypropoxy)phenyl]propane,
  (b) from about 85% to 100% of methoxyethyl methacrylate;
  said binder being capable of being polymerized upon contact with a peroxide-type free radical initiator and a t-amine type accelerator.

* * * * *

UNITED STATES PATENT OFFICE
CERTIFICATE OF CORRECTION

Patent No. 4,260,701  Dated April 7, 1981

Inventor(s) Henry L. Lee, Jr.

It is certified that error appears in the above-identified patent and that said Letters Patent are hereby corrected as shown below:

Table 6 (Column 10)

First line, first column, insert before "copolymer" ---30/70---

Column 10, line 65, cancel "178" and substitute therefor ---1/2---

Claim 1, column 15, line 9, before "weight" insert ---total---

Claim 11, column 16, line 15, cancel "t-amine-atype peroxide-type free radical initiator and a"

Column 13, line 64, cancel "alyl" and substitute therefor ---allyl---.

Signed and Sealed this

Thirtieth Day of November 1982

[SEAL]

Attest:

GERALD J. MOSSINGHOFF

Attesting Officer  Commissioner of Patents and Trademarks